(12) United States Patent
Holt

(10) Patent No.: US 10,898,689 B2
(45) Date of Patent: Jan. 26, 2021

(54) CATHETER SYSTEM AND METHOD OF INTRODUCING AN INTRAVENOUS CATHETER INTO A PATIENT

(71) Applicant: Northward Ventures, LLC, Cincinnati, OH (US)

(72) Inventor: Zachary Holt, Cincinnati, OH (US)

(73) Assignee: Northward Ventures, LLC, Cincinnati, OH (US)

(*) Notice: Subject to any disclaimer, the term of this patent is extended or adjusted under 35 U.S.C. 154(b) by 0 days.

(21) Appl. No.: 16/675,569

(22) Filed: Nov. 6, 2019

(65) Prior Publication Data
US 2020/0147349 A1 May 14, 2020

Related U.S. Application Data

(60) Provisional application No. 62/757,806, filed on Nov. 9, 2018.

(51) Int. Cl.
| | | |
|---|---|---|
| *A61M 31/00* | (2006.01) | |
| *A61M 25/06* | (2006.01) | |
| *A61M 25/09* | (2006.01) | |

(52) U.S. Cl.
CPC .... *A61M 25/0606* (2013.01); *A61M 25/0693* (2013.01); *A61M 25/09041* (2013.01)

(58) Field of Classification Search
CPC ........ A61M 25/0606; A61M 25/09041; A61M 25/0631; A61M 25/09; A61M 2025/0687;
(Continued)

(56) References Cited

U.S. PATENT DOCUMENTS

| 4,280,503 A | 7/1981 | Ackerman |
| 4,525,157 A | 6/1985 | Vaillancourt |
| (Continued) | | |

FOREIGN PATENT DOCUMENTS

| EP | 2279773 A1 | 2/2011 |
| JP | 2007-000209 A | 1/2007 |
| (Continued) | | |

OTHER PUBLICATIONS

Murata, Hiroaki, et al., "Preliminary experience with ultrasound-guided thoracic paravertebral catheterization using a catheter-over-needle-assembly," Correspondence, *Journal of Clinical Anesthesia*, 2019, 57:72-73, 2 pgs.
(Continued)

*Primary Examiner* — Rebecca E Eisenberg
(74) *Attorney, Agent, or Firm* — Frost Brown Todd LLC

(57) ABSTRACT

A catheter system and method of introducing an intravenous catheter into a patient includes a syringe, an access needle, a pliable catheter, and a guidewire. The syringe has a first chamber and a distal syringe end portion, which defines a conduit distally extending to a distal syringe opening such that the conduit fluidly connects the first chamber to the distal syringe opening. The access needle defines a needle lumen longitudinally extending therethrough and is secured relative to the distal syringe end portion. The pliable catheter is releasably secured relative to the access needle. The guidewire distally extends through the conduit toward the distal syringe opening and is configured to selectively move through the conduit, the distal syringe opening, and along the needle lumen to thereby guide movement of the pliable catheter relative to the access needle for introducing the pliable catheter into the patient.

23 Claims, 11 Drawing Sheets

(58) Field of Classification Search
CPC ............ A61M 25/0097; A61M 25/065; A61M 2025/0037; A61M 2025/0293
See application file for complete search history.

(56) References Cited

U.S. PATENT DOCUMENTS

| | | | |
|---|---|---|---|
| 4,655,750 | A | 4/1987 | Vaillancourt |
| 4,935,008 | A | 6/1990 | Lewis, Jr. |
| 4,995,866 | A | 2/1991 | Amplatz et al. |
| 5,257,979 | A | 11/1993 | Jagpal |
| 5,290,244 | A | 3/1994 | Moonka |
| 6,533,782 | B2 | 3/2003 | Howell et al. |
| 7,699,809 | B2 | 4/2010 | Urmey |
| 8,585,651 | B2 | 11/2013 | Asai |
| 8,728,035 | B2 | 5/2014 | Warring et al. |
| 8,882,713 | B1 | 11/2014 | Call et al. |
| 10,265,506 | B2 | 4/2019 | Borowicz |
| 2006/0047246 | A1 | 3/2006 | Anders |
| 2011/0152836 | A1* | 6/2011 | Riopelle ............... A61M 25/06 604/510 |
| 2013/0096428 | A1 | 4/2013 | Gillies et al. |
| 2014/0221968 | A1* | 8/2014 | Ransbury ............. A61M 39/06 604/506 |
| 2015/0224287 | A1 | 8/2015 | Bian et al. |
| 2018/0071509 | A1 | 3/2018 | Tran et al. |
| 2018/0126126 | A1 | 5/2018 | Ornelas et al. |
| 2018/0296804 | A1 | 10/2018 | Bierman |
| 2018/0369540 | A1 | 12/2018 | Asai |

FOREIGN PATENT DOCUMENTS

| | | |
|---|---|---|
| JP | 3912460 B2 | 5/2007 |
| WO | WO 98/19720 A2 | 5/1998 |
| WO | WO 98/19720 A3 | 10/1998 |

OTHER PUBLICATIONS

PowerGlide Midline Catheter, Guidelines for Use, C.R. Bard, 2014, 10 pgs.

Teleflex, Vascular Access Product Catalog, Emergency Infusion Device—EID, Teleflex Incorporated, 2018, 1 pg.

International Search Report and Written Opinion dated May 20, 2020 for International Application No. PCT/US2019/059999, 13 pages.

* cited by examiner

CATHETER SYSTEM AND METHOD OF INTRODUCING AN INTRAVENOUS CATHETER INTO A PATIENT

CROSS-REFERENCE TO RELATED APPLICATION

The application claims priority to provisional U.S. Pat. App. No. 62/757,806, filed Nov. 9, 2018, entitled "Central Venous Access Catheter System and Related Methods," the disclosure of which is hereby incorporated by reference herein.

BACKGROUND

Difficult vascular access is a common problem in healthcare. This is a daily problem in emergency medicine, affecting approximately 10% of the patient population. Increasing patient age, dialysis access, presence of cancer, frequent prior attempts, and intravenous (IV) drug abuse all affect ease of obtaining venous access. Frequently, nursing staff are unable to obtain a peripheral IV catheter. Furthermore, "PICC Teams" or "Vascular Access Teams" present within a healthcare facility are very busy and frequently take well over an hour to start attempting access on an individual patient awaiting treatment in an emergency department. These services are usually available only during normal business hours and are infrequently offered at smaller hospitals and freestanding acute care sites. This leads to delayed testing and treatment, along with increased length of stay. While emergency physicians and advanced practice providers have the ability to attempt ultrasound guided peripheral or central venous access, it may not be feasible for this to be done several times per day due to the time constraints on such healthcare providers caring for patients during an emergency shift. To this end, ultrasound guided peripheral IV catheter placement and central venous access are each a time-consuming, labor intensive process. In addition, the available ultrasound guided peripheral IV catheters are not well suited for access of central veins, such as the internal jugular or femoral veins, due to the length and relative inflexibility of the catheters, which can result in dislodgement, even after successful placement. Standard peripheral IV catheters also rely on a "flash" of blood to confirm initial access, but such a "flash" of blood is often difficult to achieve with central vein access due to the length of the catheter and/or the inability to position a tourniquet. Some central line kits include a longer single lumen catheter, but these have similar limitations. For example, central line kits often contain inflexible catheters and large bore needles such that subtle movements during placement may result in unsuccessful venous catheterization.

There is thus a need for a catheter system and method of introducing an intravenous catheter into a patient, such as for central venous access, that quickly provides access into the patient while remaining functionally placed in a desired position.

SUMMARY

One embodiment of a catheter system for accessing an anatomy of a patient includes a syringe, an access needle defining a needle lumen longitudinally extending therethrough, a pliable catheter, and a guidewire. The syringe includes a first chamber and a distal syringe end portion defining a conduit distally extending to a distal syringe opening such that the conduit fluidly connects the first chamber to the distal syringe opening. The access needle is releasably secured relative to the distal syringe end portion such that the access needle distally projects from the distal syringe end portion. The pliable catheter is releasably secured relative to the access needle such that the access needle is received within the pliable catheter. In addition, the guidewire is configured to selectively move through the conduit, the distal syringe opening, and along the needle lumen to thereby guide movement of the pliable catheter relative to the access needle for introducing the pliable catheter into the patient.

One embodiment of a kit catheter system for accessing an anatomy of a patient includes an access needle defining a needle lumen longitudinally extending therethrough, a pliable catheter, and a guidewire. The syringe includes a first chamber and a distal syringe end portion defining a conduit distally extending to a distal syringe opening such that the conduit fluidly connects the first chamber to the distal syringe opening. The access needle is configured to be releasably secured relative to the distal syringe end portion such that the access needle distally projects from the distal syringe end portion. The pliable catheter is configured to be releasably secured relative to the access needle such that the access needle is received within the pliable catheter. In addition, the guidewire is configured to selectively move through the conduit, the distal syringe opening, and along the needle lumen to thereby guide movement of the pliable catheter relative to the access needle for introducing the pliable catheter into the patient.

In use, one embodiment of a method of introducing a pliable catheter into a patient with a catheter system includes guiding the pliable catheter distally along the guidewire thereby introducing the pliable catheter into an anatomy of the patient.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
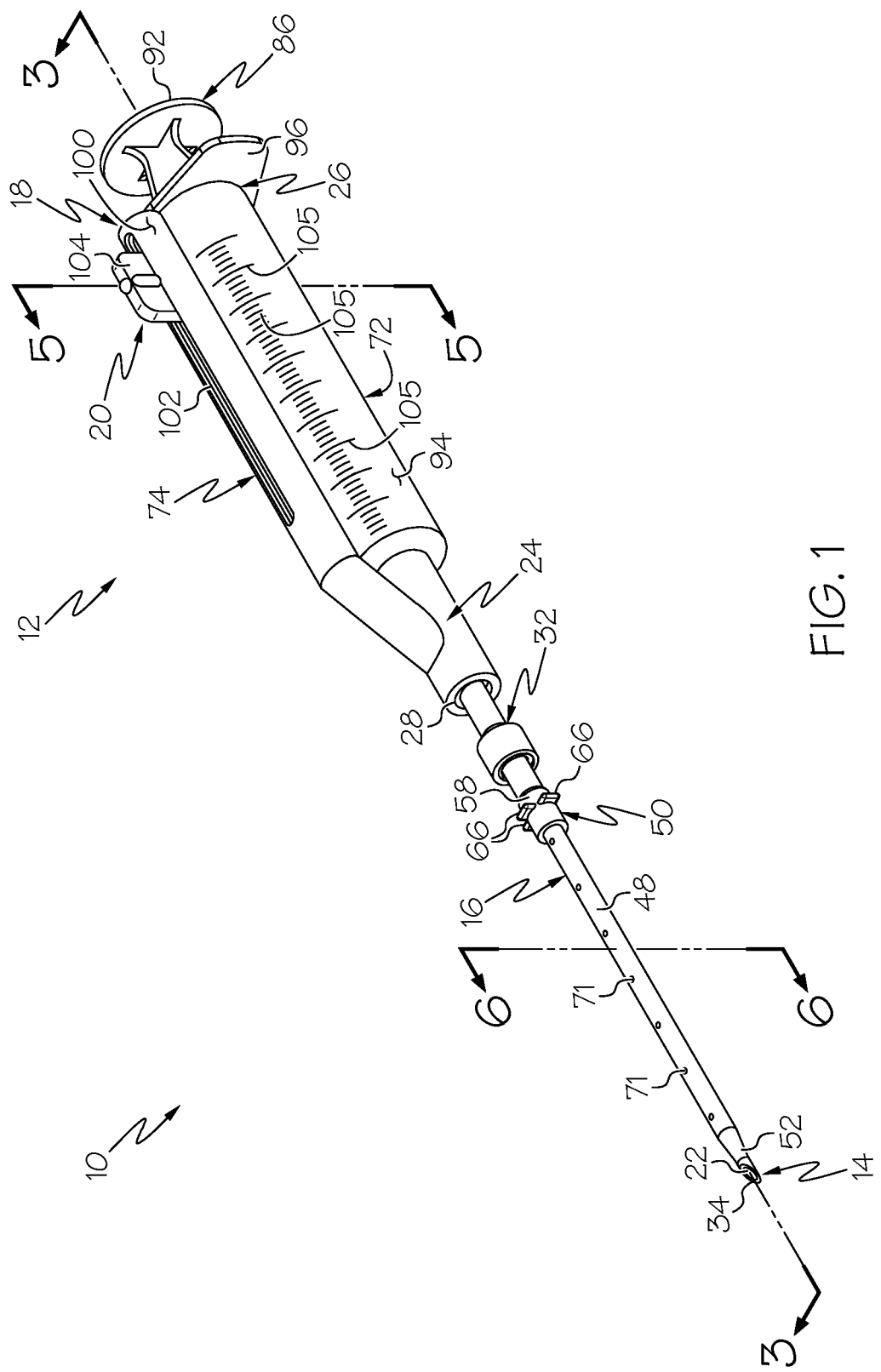
FIG. 1 depicts a perspective view of a first exemplary embodiment of a catheter system including a first example of a pliable catheter, a first example of an access needle, and a first example of a syringe for introducing the pliable catheter into a patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator of a catheter system. The term "proximal" refers to the position of an element closer to the operator of the catheter system and further away from an end of a catheter. The term "distal" refers to the position of an element closer to the end of the catheter and further away from the operator of the catheter system. It will be further appreciated that, for convenience and clarity, spatial terms such as "under," "above," "longitudinal," and "transverse" also are used herein for reference to relative positions and directions. Such terms are used below with reference to views as illustrated for clarity and are not intended to limit the invention described herein.

I. EXEMPLARY CATHETER SYSTEMS FOR ACCESSING AN ANATOMY OF A PATIENT

Figure 2:
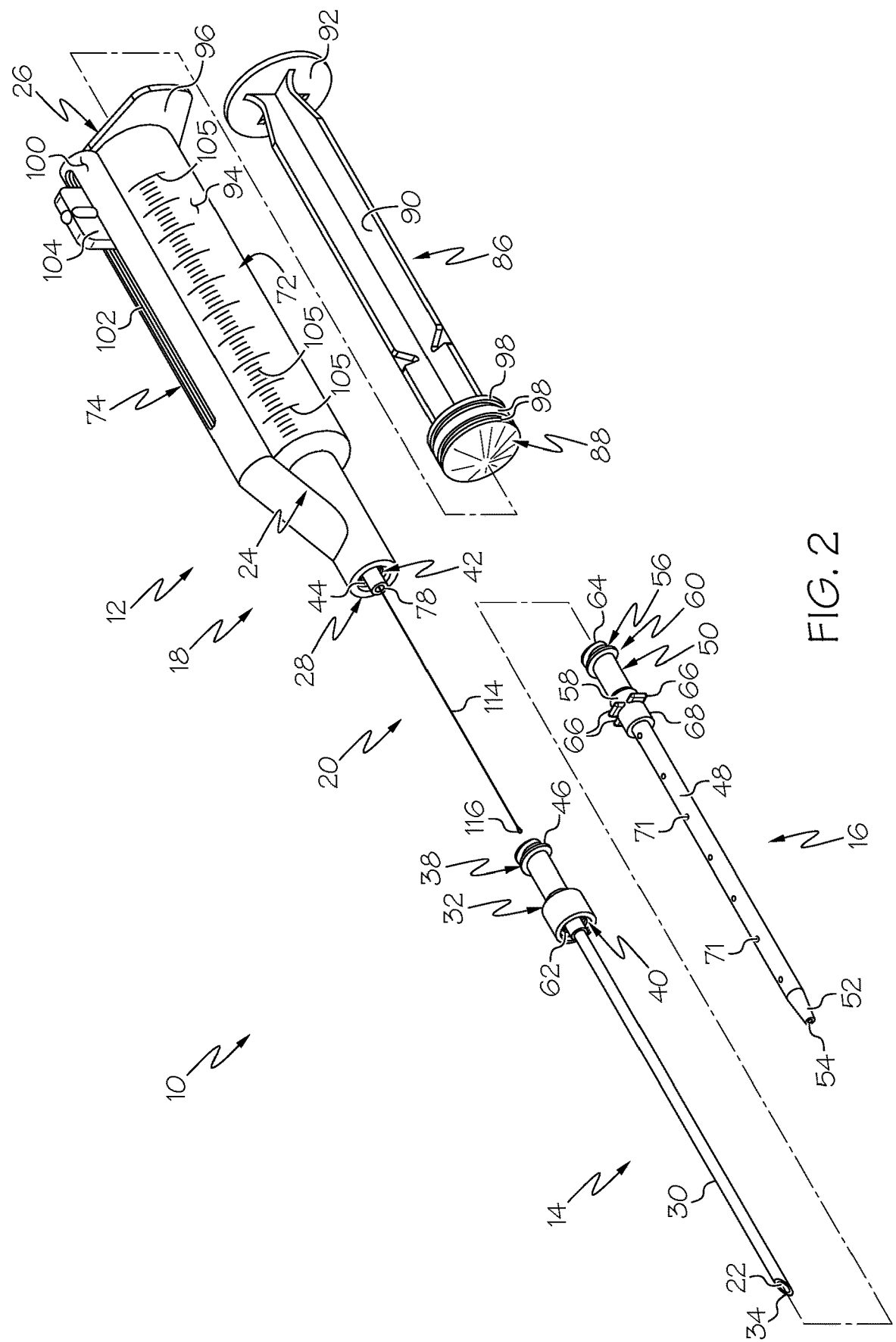
FIG. 2 depicts an exploded, perspective view of the catheter system of FIG. 1.

FIGS. 1-2 show a first exemplary embodiment of a catheter system (10) including a first example of a syringe assembly (12) with a first example of an access needle (14) projecting distally therefrom supporting a first example of a pliable catheter (16) configured to be inserted into an anatomy of a patient and positioned for fluidic access to the anatomy as desired by an operator, such as a healthcare professional. To this end, syringe assembly (12) has a syringe (18) and an operatively connected guidewire (20) configured to be selectively moved through a needle lumen (22) of access needle (14) to distally exit and project from access needle (14) for positioning in the anatomy. Once guidewire (20) is positioned as desired in the anatomy, pliable catheter (16) is configured to release from syringe assembly (12) while guidewire (20) guides introduction of pliable catheter (16) into the desired position for accessing the anatomy. In one example as discussed below in greater detail, such anatomy is a central vein of the patient such that the pliable catheter (16) in fluid communication with the central vein may also be referred to herein as a "central venous catheter," a "central vein catheter," or a "CVC." Once introduced into the patient, the operator removably secures pliable catheter (16) relative to the patient and withdraws guidewire (20) and access needle (14) via syringe (18) as discussed below in greater detail. Materials that can form one or more portions of catheter system (10) include polyurethane and/or silicone although it will be appreciated that any similar materials known for use as a central line may be additionally or alternatively used. While such anatomy of the patient is discussed in the present example as the central vein, it will be appreciated that any such catheter system described herein, such as catheter system (10), may be similarly used to access any anatomy of any patient for fluid connection therewith. The invention is thus not intended to be unnecessarily limited to use with the central vein. As used herein, the term "pliable" refers to being generally flexible so as to be rigid enough for insertion into the patient while still allowing for sufficient bending along the geometries of the anatomy and overall patient comfort and use. Indeed, the term "pliable" thus broadly includes any such flexibility for positioning in the patient and is not intended to unnecessarily limit the invention described herein.

Figure 3:
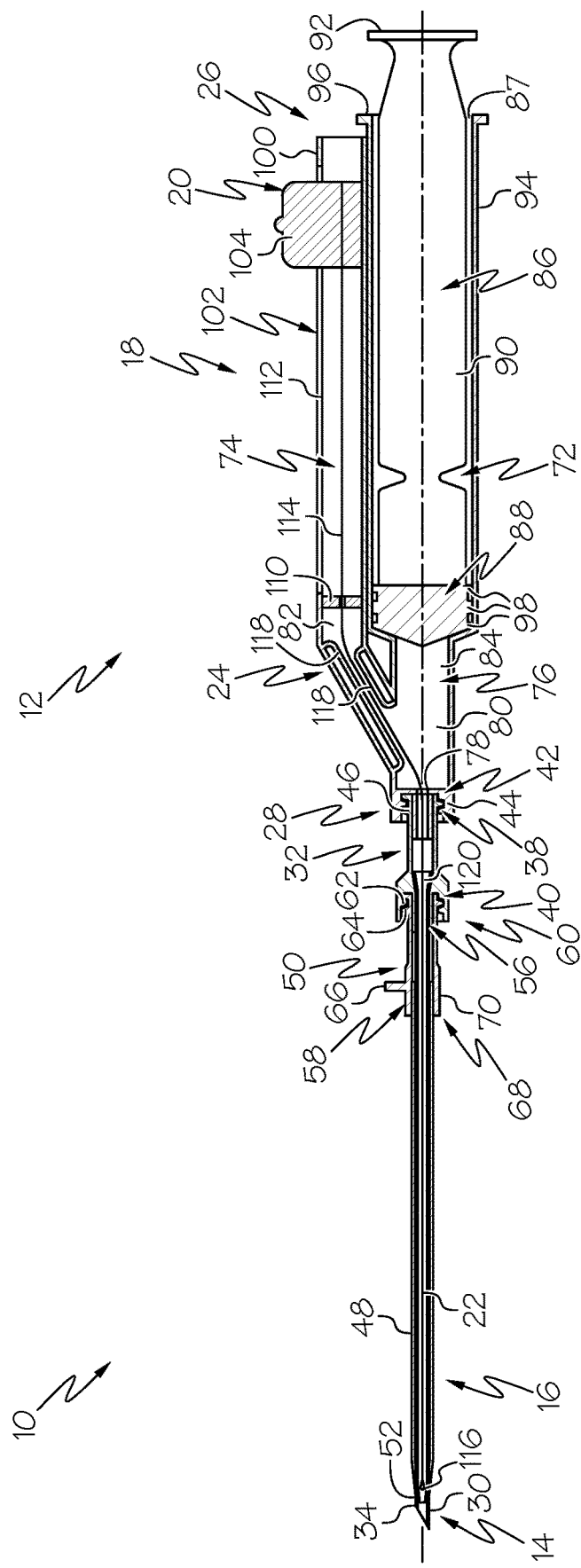
FIG. 3 depicts a cross-sectional view of the catheter system of FIG. 1 taken along section line 3-3 of FIG. 1.

With respect to FIGS. 2-3, syringe (18) has a distal syringe end portion (24) configured to secure relative to access needle (14) and pliable catheter (16) and a longitudinally opposing proximal syringe end portion (26) configured to be gripped and manipulated by the operator for introducing the pliable catheter (16) into the patient. In the present example, access needle (14) releasably secures directly to distal syringe end portion (24) via a syringe coupling (28). More particularly, access needle (14) has a generally rigid needle body (30) distally extending from a needle adapter (32) to a distal needle tip (34), which is tapered, and more particularly beveled, in the present example and configured to puncture patient tissue. Alternatively, a thin dilator (not shown) may overlie access needle (14) transversely under pliable catheter (16) in order to decrease in diameter thus tapering toward distal needle tip (34) for easing insertion of access needle (14) with pliable catheter (16) into the patient. Needle body (30) is generally cylindrical and defines a needle lumen (22) extending along a longitudinal lumen axis therethrough. Needle adapter (32) rigidly secures to needle body (30) and includes a proximal needle connection (38) positioned at proximal end of needle adapter (32) and distally extends to a distal needle connection (40) at a distal end of needle adapter (32). Proximal needle connection (38) releasably secures to a distal syringe connection (42) on distal syringe end portion (24) thereby fluidly connecting needle lumen to distal syringe end portion (24) as discussed below in greater detail. Proximal needle connection (38) and distal syringe connection (42) thus define syringe coupling (28).

More particularly, in the present example, distal syringe connection (42) includes a female luer lock (44) configured to rotatably receive a male luer lock (46) of proximal needle connection (38) for threaded engagement therebetween. Of course, alternative connections to luer locks (44, 46) may be similarly used and the invention is not intended to be unnecessarily limited to such luer locks (44, 46). Moreover, while the present example of access needle (14) depicts beveled distal needle tip (34) and needle body (30) of a predetermined longitudinal length and predetermined gauge for accessing the central vein, any desired length and gauge may be similarly used in an alternative access needle for accessing one or more portions of the anatomy of the patient. The invention is thus not intended to be unnecessarily limited to the length and gauge of access needle (14) shown and described herein.

Furthermore, pliable catheter (16) of the present example releasably secures directly to access needle (14) such that pliable catheter (16) receives access needle (14). In turn, access needle (14) stiffens pliable catheter (16) for insertion into the patient as discussed below in greater detail. Relative to access needle (14), pliable catheter (16) is generally less rigid and more flexible with a catheter body (48) extending distally from a catheter adapter (50) to a distal catheter tip (52), which is frustoconically tapered in the present example to ease insertion in the patient following puncture by distal needle tip (34). Catheter body (48) is generally cylindrical and defines a catheter lumen (54) extending along the longitudinal lumen axis therethrough. Alternatively, in another example, catheter lumen (54) may define additional lumens (not shown), such as two or three lumens (not shown) for additional access into the anatomy of the patient. In still another example, an integrated extension line (not shown) may be incorporated into catheter system (10), such as by a fluid connection near catheter adapter (50) being configured to connect to an intravenous line (not shown) and/or another syringe (not shown). Catheter adapter (50) is secured to catheter body (48) and includes a proximal catheter connection (56) positioned at proximal end of catheter adapter (50) and distally extends to a catheter hub (58) at a distal end portion of catheter adapter (50). Proximal catheter connection (56) releasably secures to distal needle connection (40) on access needle (14) thereby securing pliable catheter (16) to access needle (14) relative to distal syringe end portion (24). Proximal catheter connection (56) and distal needle connection (40) thus define a distal catheter coupling (60).

More particularly, in the present example, distal needle connection (40) includes a female luer lock (62) configured to rotatably receive a male luer lock (64) of proximal catheter connection (56) for threaded engagement therebetween. Threading of male and female luer locks (64, 62) associated with pliable catheter (16) may be reversed relative to threading of male and female luer locks (46, 44) associated with access needle (14) in order to rotatably isolate removal of pliable catheter (16) from access needle (14). For example, the operator may be able to more easily rotatably remove pliable catheter (16) with reversed threading relative to syringe (18) during use without inadvertently removing access needle (14) relative to syringe (18) via the reversed threading on male and female luer locks (64, 62). Once removed and placed in the patient, male luer lock (64) is available for connection and fluidly sealing with IV tubing, a syringe, and any other compatible luer connection for administration of medications, IV fluids, or radiologic contrast materials or even for removal of material from an accessed portion of the patient, such as blood, air, and/or ascites. Of course, alternative connections to luer locks (62, 64) may be similarly used and the invention is not intended to be unnecessarily limited to such luer locks (62, 64). Moreover, while the present example of pliable catheter (16) depicts tapered distal catheter tip (52) and catheter body (48) of a predetermined longitudinal length from about 5 centimeters to about 12 centimeters and a predetermined gauge for accessing the central vein, any desired length and gauge may be similarly used in an alternative access needle for accessing one or more portions of the anatomy of the patient. The invention is thus not intended to be unnecessarily limited to the length and gauge of pliable catheter (16) shown and described herein. Still, while lengths and gauges of pliable catheter (16) as well as access needle (14) may vary, access needle (14) is generally longer than pliable catheter (16) while secured therein such that distal needle tip (34) distally projects from distal catheter tip (52) for puncturing tissue prior to insertion of pliable catheter (16) into the patient.

In the present example, catheter adapter (50) further includes a plurality of projections (66) radially extending from and angularly positioned about catheter hub (58). Projections (66) are collectively configured to be grasped by the operator while inhibiting contact with the patient. More particularly, this plurality of projections (66) includes three such projections (66) configured to be grasped and manipulated by the operator for distally advancing pliable catheter (16) relative to access needle (14) in use, but it will be appreciated that an alternative number of projections (66) may be similarly used. In one example, projections (66) may also be used to engage a specialized locking dressing (not shown) to thereby secure the locking dressing (not shown) in place relative to the patient. In this respect, the locking dressing (not shown) is configured to be releasably secured to a portion of pliable catheter (16), such as catheter hub (58). The locking dressing (not shown) may thus vary in size, shape, and securement as desired for accommodating pliable catheter (16) or any alternative pliable catheter (not shown). The specialized locking dressing (not shown) may reduce the likelihood, or even eliminate, suturing in some instances. In addition, a gap portion (68) on catheter hub (58) remains free of such projections (66) in the present example to be placed against the patient for greater comfort. Gap portion (68) thus includes a continuous surface (70) without projections (66) and, in one example, is substantially planar.

In order to aid with placement of pliable catheter (16), catheter system (10) of the present example further includes a catheter indicia (71) positioned on pliable catheter (16). Catheter indicia (71) of the present example includes a series of longitudinally spaced circles indicative of depth of insertion into the patient relative to distal catheter tip (52). Such catheter indicia (71) may also include a hyperdense ultrasound material strip for enhanced identification in the patient via ultrasound. Of course, any such indicia may be similarly used such that the invention is not intended to be unnecessarily limited to the particular catheter indicia (71) shown in the present example.

With continued reference to FIGS. 2-3 syringe assembly (12) includes syringe (18) having distal syringe end portion (24) and guidewire (20) as briefly discussed above. To this end, syringe (18) includes a vacuum chamber (72) and a guidewire chamber (74) for respectively generating a vacuum and manipulating guidewire during use. Vacuum and guidewire chambers (72, 74) of the present example proximally extend from distal syringe end portion (24) and are transversely offset relative to each other. More particularly, vacuum and guidewire chambers (72, 74) respectively define longitudinal chamber axes in parallel with each other. Vacuum chamber (72) of the present example is shown as coaxial with the longitudinal lumen axis of needle lumen (22) whereas guidewire chamber (74) is transversely offset from the longitudinal lumen axis of needle lumen (22) while access needle (14) is secured to syringe (18). Alternatively, vacuum and guidewire chambers (72, 74) may be alternatively positioned relative to access needle (14) such that the invention is not intended to be unnecessarily limited to the particular arrangement of vacuum and guidewire chambers (72, 74) shown in the present example.

Distal syringe end portion (24) further includes a conduit (76) distally extending to a distal syringe opening (78), which is surrounded by female luer lock (44) in the present example. Conduit (76) connects each of vacuum and guidewire chambers (72, 74) to distal syringe opening (78) for further communication into needle lumen (22) during use. More particularly, conduit (76) includes a distal lumen (80) directly connected to distal syringe opening (78), a proximal guidewire lumen (82) directly connected to guidewire chamber (74), and a proximal vacuum lumen (84) directly connected to vacuum chamber (72). Proximal guidewire lumen (82) and proximal vacuum lumen (84) distally extend from respective guidewire and vacuum chambers (74, 72) and intersect at distal lumen (80) in a Y-shaped configuration for communication with distal syringe opening (78), although it will be appreciated that any configuration for communicating fluid and/or guidewire (20) through distal syringe opening (78) may be similarly used. In one example, conduit (76) may be filled with a liquid, such as sterile water or saline, prior to use in order to reduce, or even eliminate, air in conduit (76) and vacuum chamber (72).

Given that vacuum chamber (72) is configured to sustain and communicate a vacuum through conduit (76) and into needle lumen (22) during use, syringe (18) of the present example further includes a vacuum generator, such as a vacuum plunger (86). Vacuum plunger (86) is configured to be translatably received through a proximal opening (87) into vacuum chamber (72) and includes a stopper (88), a rod (90) proximally extending from stopper (88), and a proximal flange (92) proximally and radially extending from rod (90). Stopper (88) fluidly seals against a sidewall (94) of vacuum chamber (72) such that withdrawing stopper (88) proximally through vacuum chamber (72) generates the vacuum at conduit (76). Proximal flange (92) is configured to be gripped and manipulated by the operator such that proximally pulling proximal flange (92) relative to vacuum chamber (72) similarly pulls on rod (90) to proximally translate stopper (88). In addition, syringe (18) of the present example also includes another flange (96) extending from sidewall (94) at a proximal end thereof to provide the operator with additional grip for manipulating proximal flange (92) relative to flange (96). Stopper (88) of the present example is generally resilient rubber, silicone, or any other material configured to provide a fluid seal and inhibit leakage therethrough. Stopper (88) more particularly has a series of annular seals (98) configured to engage and fluidly seal against sidewall (94), although it will be appreciated that any number of such seals (98) may be similarly used. Vacuum plunger (86) may alternatively be distally urged through vacuum chamber (72) to generate pressure within vacuum chamber (72) for discharging fluid through conduit (76) and distal syringe opening (78) as desired. Vacuum chamber (72) may thus contain negative or positive pressure as desired by the operator. Moreover, any vacuum or pressure generating device may be similarly used for creating negative or positive pressure within vacuum chamber (72) such that the invention is not intended to be unnecessarily limited to use with vacuum plunger (86).

As discussed below in greater detail, guidewire (20) is movable from a proximal guidewire position, which is shown in FIGS. 2-3, to a distal guidewire position. Guidewire chamber (74) generally contains at least a portion of guidewire (20) extending coaxially along the longitudinal chamber axis of guidewire chamber (74) such that guidewire (20) remains confined when not in use, but available for movement and positioning as desired by the operator. Guidewire chamber (74) of the present example more particularly includes a sidewall (100) extending along sidewall (94) of vacuum chamber (72) so that the operator may easily and simultaneously grip the vacuum and guidewire chambers (72, 74). In order to access and direct movement of guidewire (20), an elongate slot (102) through sidewall (100) extends longitudinally such that guidewire (20) may be similarly moved distally and proximally through guidewire chamber (74) between the proximal and distal guidewire positions. Syringe assembly (12), as shown in the present example, further includes a handle (104) fixed to a proximal end portion of guidewire (20) that transversely extends from guidewire (20) and through elongate slot (102) to be gripped and manipulated by the operator. Thus, handle (104) is positioned in a proximal portion of elongate slot (102) while guidewire (20) is in the proximal guidewire position. In contrast, distally urging handle (104) to a distal portion of elongate slot (102) similarly positions guidewire (20) in the distal guidewire position.

In order to aid with placement guidewire (20) and/or vacuum plunger (86), catheter system (10) of the present example further includes a syringe indicia (105) positioned on syringe (18). More particularly, syringe indicia (105) includes a series of longitudinally spaced markings indicative of a volume of fluid within vacuum chamber (72) contained against stopper (88). Alternatively or in addition, syringe indicia (105) may also include a series of longitudinally spaced markings indicative of the position of distal guidewire tip (116) relative to distal needle tip (34) based on alignment of handle (104) with syringe indicia (105). Of course, any such indicia may be similarly used such that the invention is not intended to be unnecessarily limited to the particular syringe indicia (105) shown in the present example. Furthermore, vacuum chamber (72) of the present example is formed from material allowing sufficient light therethrough to communicate to the operator that a fluid, such as a bodily fluid, including a gas or a liquid, has been received therein. For example, such material of sidewall (94) defining vacuum chamber (72) may be translucent or even transparent. The remaining portions of syringe (18), such as distal syringe end portion (24) may be similarly translucent or even transparent in one example.

During movement of guidewire (20), handle (104) includes a lower flange (106) slidably received within a track channel (108) defined by sidewall (100) within guidewire chamber (74). With respect to FIGS. 4-6, track channel (108) generally captures lower flange (106) in transverse directions, while allowing for longitudinal movement of lower flange (106) therethrough. In turn, track channel (108) guides movement of lower flange (106) while retaining guidewire (20) along the chamber axis of guidewire chamber (74). Of course, alternative structures configured to guide movement of handle (104) through guidewire chamber (74) may be similarly used. In the present example, syringe assembly (12) also includes an annular fluid seal (110) positioned between guidewire chamber (74) and proximal guidewire lumen (82) of conduit (76) as well as an elongate fluid seal (112) in elongate slot (102). Similar to handle (104), annular fluid seal (110) supports guidewire (20) along the chamber axis of guidewire chamber (74) while also fluidly sealing guidewire chamber (74) from proximal guidewire lumen (82) of conduit (76) in or to inhibit bodily fluid of the patient, such as blood, from leaking from the conduit (76) and into guidewire chamber (74). In the event that such bodily fluid leaks proximally through annular fluid seal (110) and into guidewire chamber (74), elongate fluid seal (112) is configured to inhibit leakage from guidewire chamber (74) while still allowing for movement of handle (104) extending through elongate fluid seal (112). Materials that may form such seals (110, 112) include resilient rubber, silicone, or any other material configured to provide a fluid seal and inhibit leakage therethrough.

Figure 4:
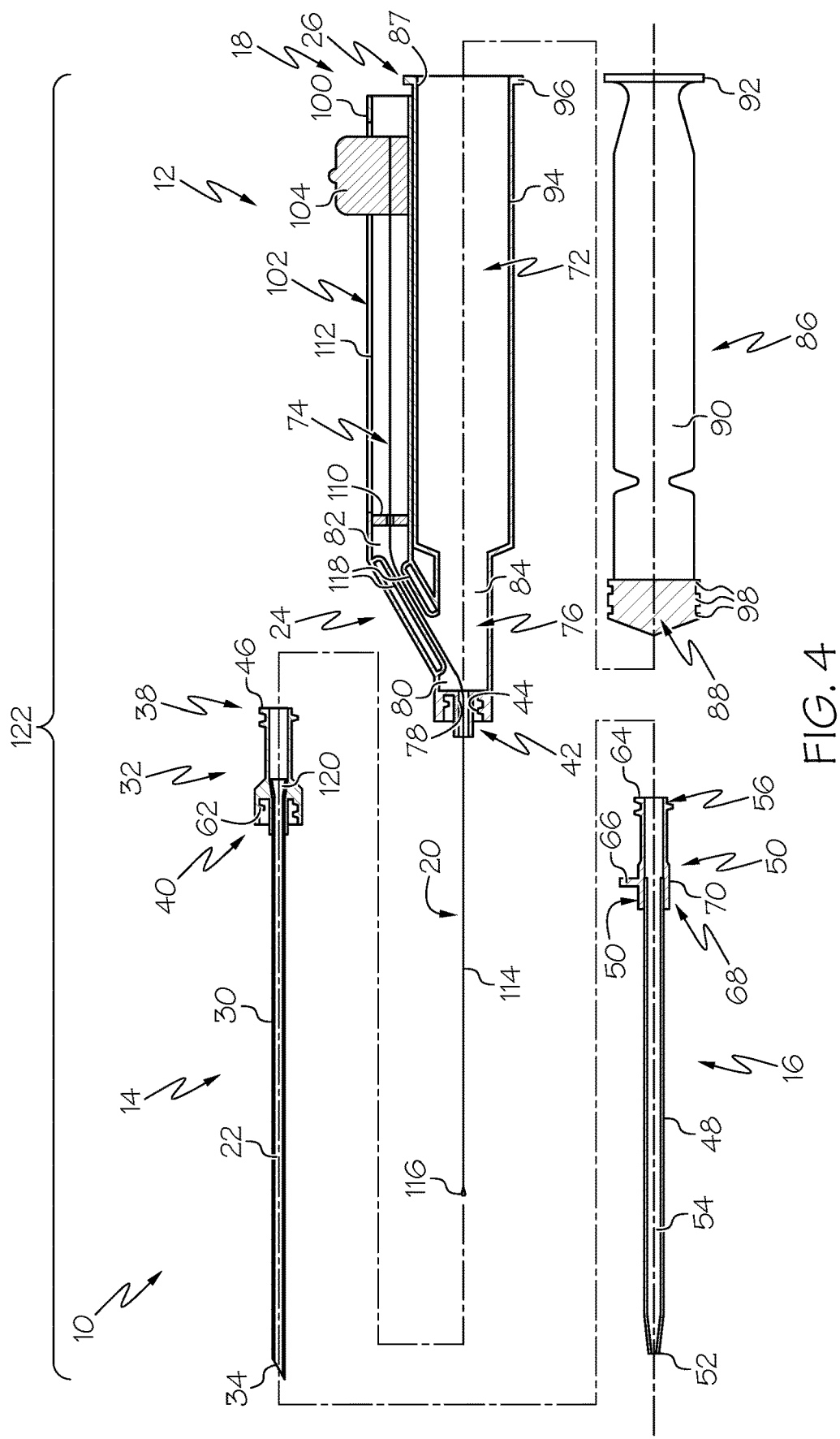
FIG. 4 depicts an exploded, cross-sectional view of the catheter system of FIG. 1 taken along section line 3-3 of FIG. 1.
Figure 5:
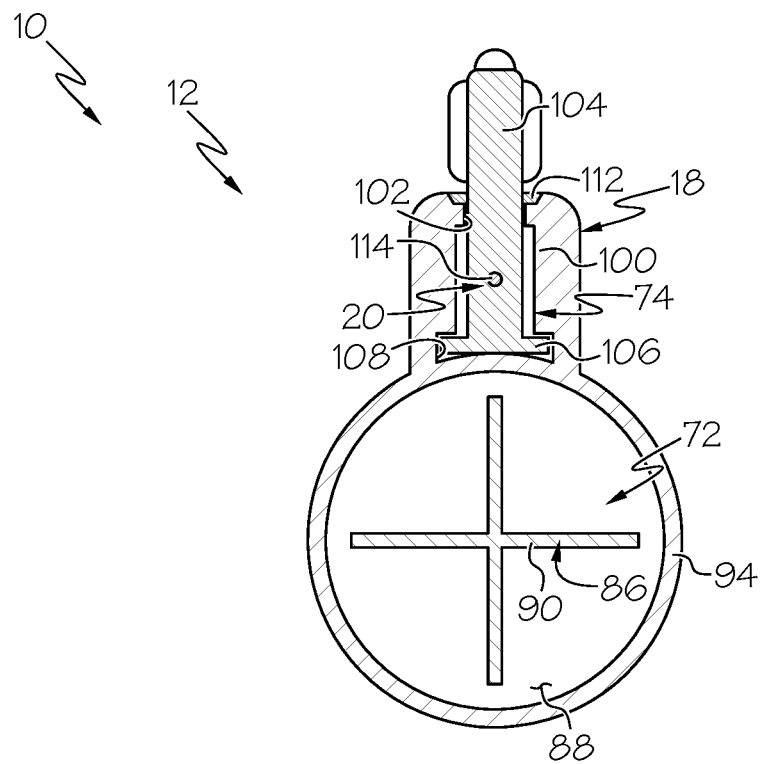
FIG. 5 depicts a cross-sectional view of the catheter system of FIG. 1 taken along section line 5-5 of FIG. 1.
Figure 6:
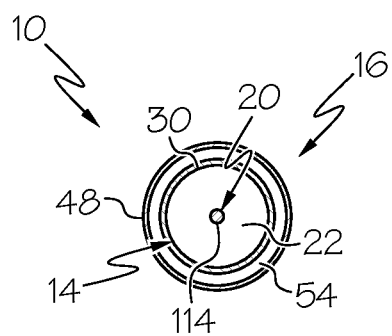
FIG. 6 depicts a cross-sectional view of the catheter system of FIG. 1 taken along section line 6-6 of FIG. 1.

With continued reference to FIGS. 4-6, guidewire (20) includes an elongate guidewire body (114) distally extending from handle (104) to a distal guidewire tip (116). Distal guidewire tip (116) of the present example, is an atraumatic tip having a tear-drop shape configured to inhibit inadvertently damaging or entangling with tissue, such as vascular structures, or devices, including, but not limited to, pacemaker leads or dialysis catheters, during use. Guidewire body (114) of the present example may be formed with a variable stiffness, tapered metal wire, such as a nitinol material, although it will be appreciated that alternative materials and arrangements for guidewire body (114), such as steel, solid core, hollow core, or coil wires may be similarly used. Alternatively, in other examples, distal guidewire tip (116) may have a ball-shape or J-shape as desired by the operator for use. The invention is thus not intended to be unnecessarily limited to guidewire body (114) shown and described herein.

In the proximal guidewire position, distal guidewire tip (116) remains transversely surrounded by access needle (14) within needle lumen (22), whereas distal guidewire tip (116) protrudes from access needle (14) in the distal guidewire position. Various features are configured to guide translation of guidewire (20) while moving guidewire (20) between distal and proximal guidewire positions. As noted above, handle (104) pushes or pulls guidewire (20) as directed by the operator while handle (104) and annular fluid seal (110) retain a portion of guidewire body (114) along the chamber axis within guidewire chamber (74). In one example, proximal guidewire lumen (82) of conduit (76) has narrowed sidewalls (118) configured to guide another portion of guidewire body (114) from the chamber axis within guidewire chamber (74) toward distal syringe opening (78) to the longitudinal lumen axis of needle lumen (22), although alternative structural arrangements for guiding guidewire body (114) may be similarly used. Needle body (30) within needle adapter (32) also includes a needle body mouth (120) that tapers outward in the proximal direction so as to enlarge this portion of needle lumen (22) for guiding yet another portion of guidewire body (114) through access needle (14) and inhibit catching, snagging, twisting, bending, or kinking of guidewire (20) during movement.

While the above description is directed to one arrangement of catheter system (10) assembled for use, syringe assembly (12), access needle (14), and pliable catheter (16) may also be disassembled, entirely or partially, as components of a catheter system kit (122). In addition to the components of catheter system (10) discussed above, catheter system kit (122) in one example further includes a luer lock cap, a chlorhexidine gluconate and isopropyl alcohol applicator, such as that sold under the brand CHLORAPREP™, a small sterile drape with a rectangular adhesive opening, the above referenced anchoring locking dressing, a short sterile ultrasound probe cover, sterile ultrasound gel, and/or a mask with facemask and elastic ear loops. A sealed lidocaine vial or prefilled lidocaine syringe may also be included in one example.

Figure 7:
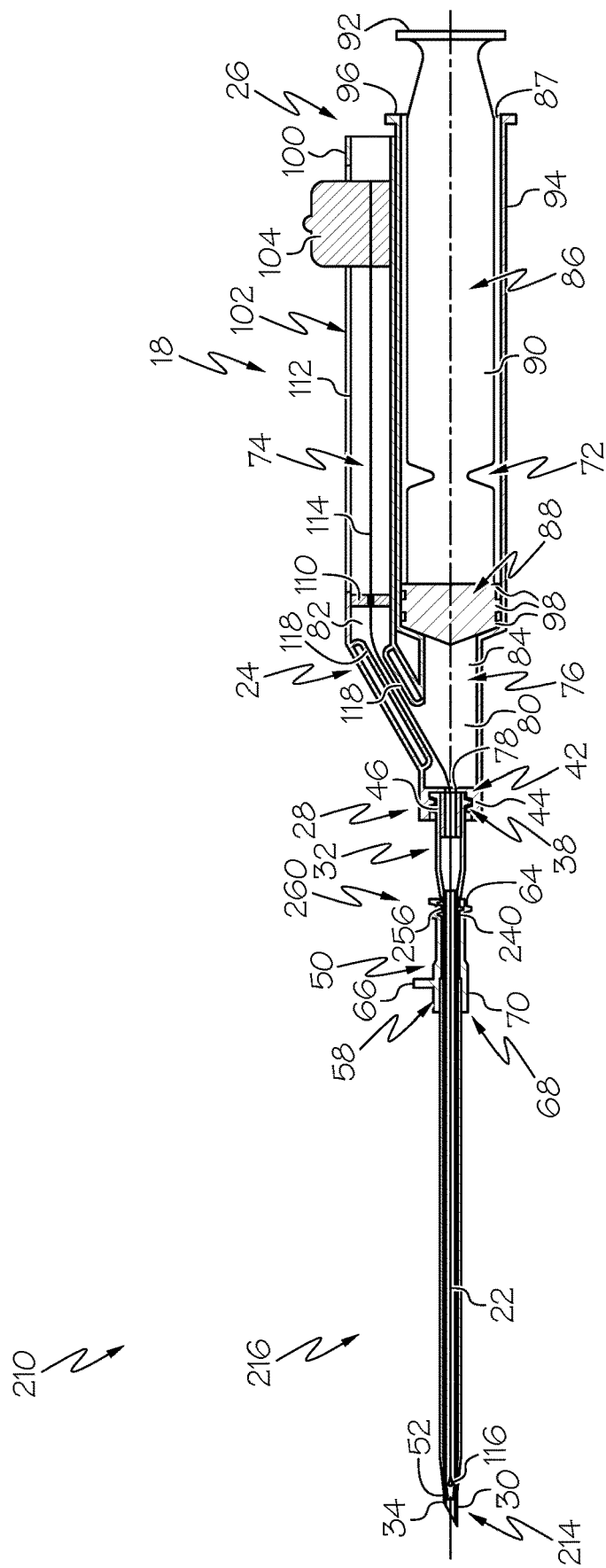
FIG. 7 depicts a cross-sectional view of a second exemplary embodiment of a catheter system taken along a centerline thereof including a second example of a pliable catheter, a second example of an access needle, and the syringe of FIG. 1 for introducing the pliable catheter into a patient.
Figure 8:
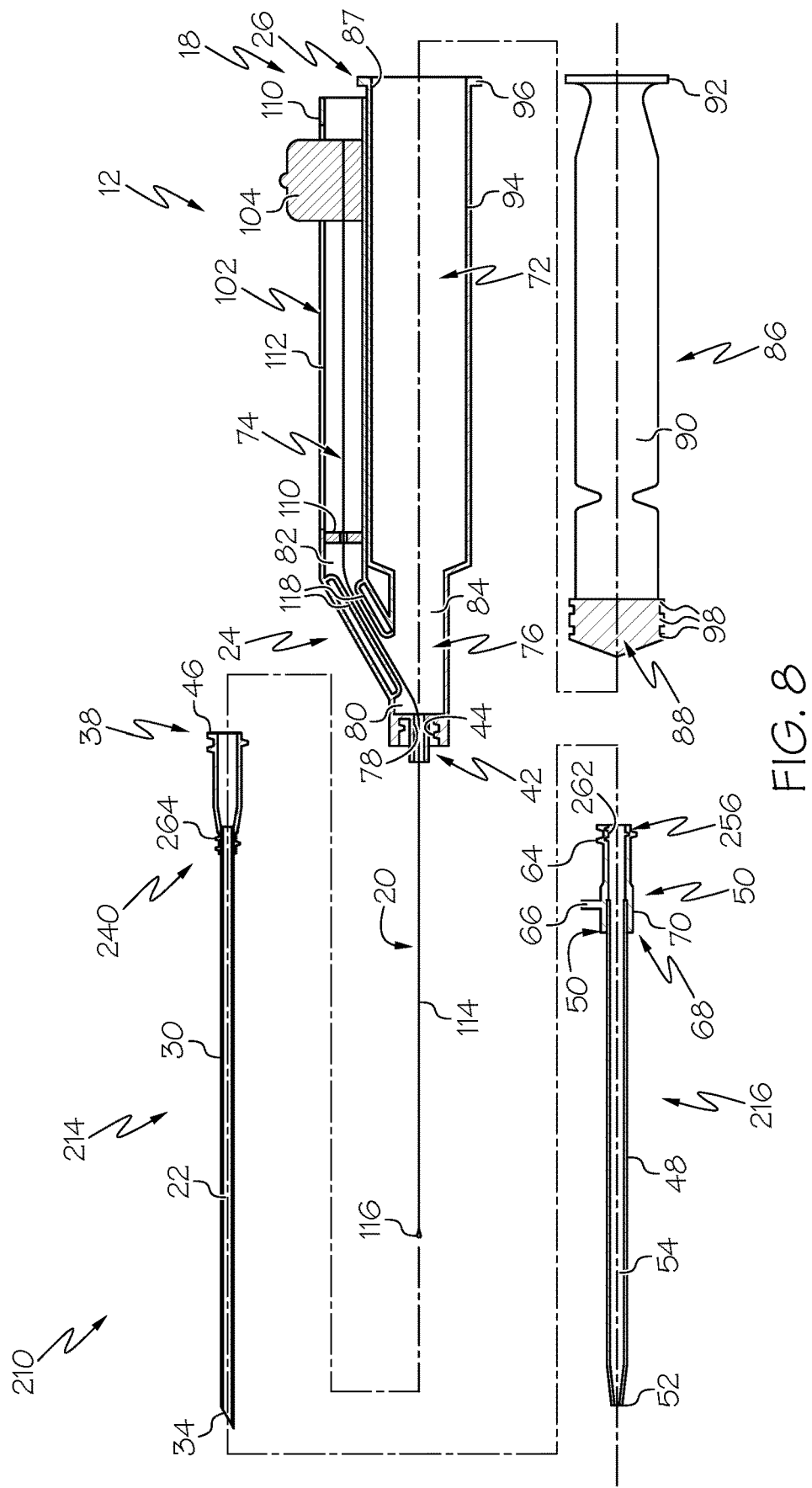
FIG. 8 depicts an exploded, cross-sectional view of the catheter system of FIG. 7 taken along the centerline thereof.

FIGS. 7-8 show a second exemplary embodiment of a catheter system (210) having syringe assembly (12) discussed above in greater detail for use with a second example of an access needle (214) and a second example of a pliable catheter (216). Rather than distal catheter coupling (60) (see FIG. 4) with cooperating luer locks (62, 64) (see FIG. 4), catheter system (210) has an alternative distal catheter coupling (260) with a female friction lock (262) configured to receive a male friction lock (264) for releasably securing pliable catheter (216) to access needle (214). By way of further example, female and male friction locks (262, 264) may alternatively be female and male rotational locks that are smaller than luer locks (62, 64) discussed above, but are rotatably coupled and decoupled similar to that of luer locks (62, 64). In this respect distal catheter coupling (260) is not intended to be unnecessarily limited to female and male friction locks (262, 264). Unless otherwise stated herein, catheter system (210) has like structure for functioning as catheter system (10) (see FIG. 4), and like numbers used below indicate like features discussed above in greater detail.

With respect to FIGS. 7-8, access needle (214) of the present example has a distal needle connection (240), and pliable catheter (216) has a proximal catheter connection (256) such that distal needle connection (240) and proximal catheter connection (256) collectively define distal catheter coupling (260). More particularly, distal needle connection (240) includes male friction lock (264), whereas proximal catheter connection (256) includes female friction lock (262). Rather than rotatably connect together, male friction lock (264) slides into engagement or disengagement with female friction lock (262) as desired by the operator. Male friction lock (264) has outer threading configured to longitudinally engage and overlap with female friction lock (262) for securing pliable catheter (216) to access needle (214). In order to withdraw access needle (214) from pliable catheter (216), the operator distally urges pliable catheter (216) relative to access needle (214) with sufficient force to overcome and deflect the outer and/or inner threadings until female friction lock (262) fully releases male friction lock (264). Such translation of pliable catheter (216) relative to access needle (214) may isolate removal of pliable catheter (216) from access needle (214). For example, the operator may be able to more easily translatably remove pliable catheter (216) relative to syringe (18) during use without inadvertently removing access needle (214) relative to syringe (18). Of course, alternative connections to friction locks (262, 264) may be similarly used, and various mechanisms for releasing such locks, including, but not limited to, a button release, may be incorporated into catheter system (210) such that the invention is not intended to be unnecessarily limited to friction locks (262, 264) of the present example. Once removed and placed in the patient, pliable catheter (216), like pliable catheter (16) discussed above, also includes male luer lock (64) for connection and fluidly sealing with any compatible luer connection as discussed above.

Figure 9:
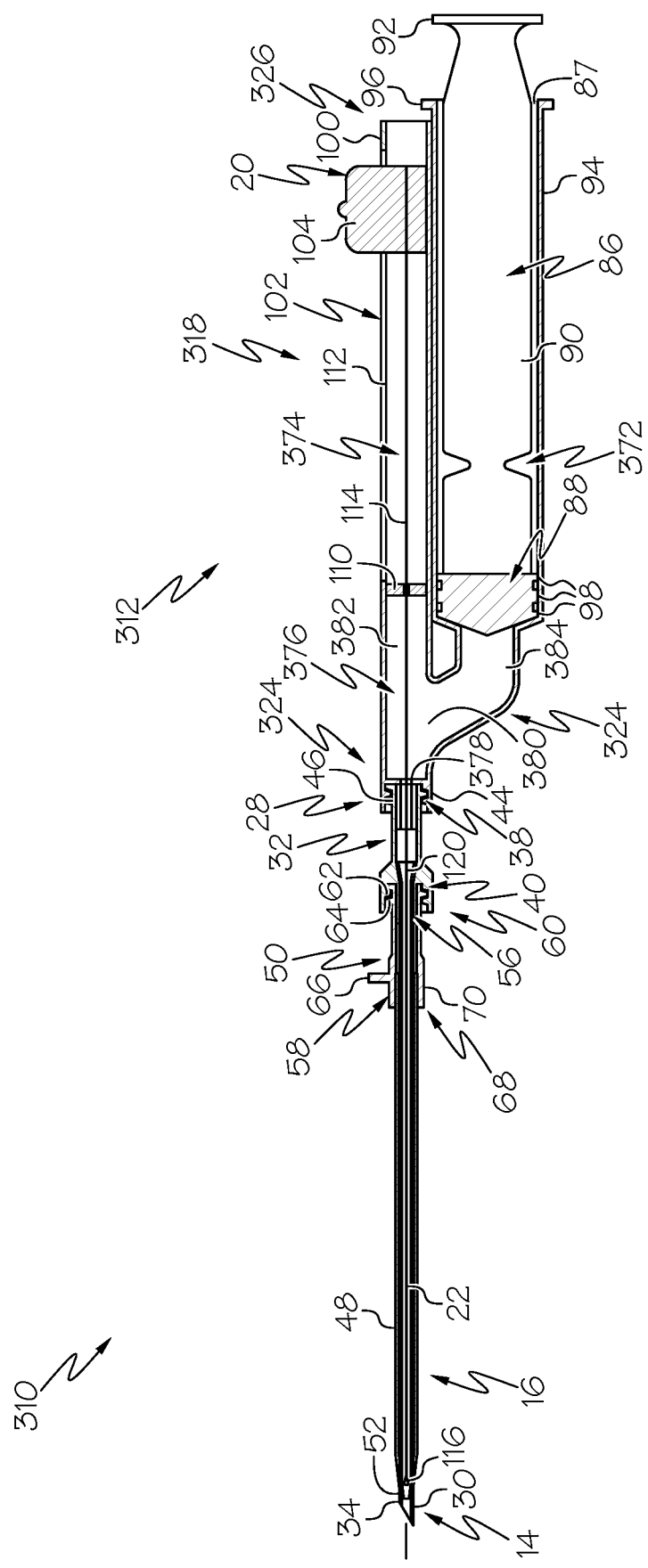
FIG. 9 depicts a cross-sectional view of a third exemplary embodiment of a catheter system taken along a centerline thereof including the pliable catheter and the access needle of FIG. 1 and a second example of a syringe for introducing the pliable catheter into a patient.

FIG. 9 shows a third exemplary embodiment of a catheter system (310) having access needle (14) and pliable catheter (16) discussed above in greater detail for use with a second example of a syringe assembly (312). Rather than having vacuum chamber (72) (see FIG. 4) longitudinally aligned with needle lumen (22), catheter system (310) has an alternative syringe (318) with an alternative guidewire chamber (374) longitudinally aligned with needle lumen (22) and an alternative vacuum chamber (372) transversely offset from guidewire chamber (374) and needle lumen (22). Unless otherwise stated herein, catheter system (310) has like structure for functioning as catheter system (10) (see FIG. 4), and like numbers used below indicate like features discussed above in greater detail.

To this end, syringe (318) of syringe assembly (312) proximally extends from a distal syringe end portion (324) to a proximal syringe end portion (326). Vacuum and guidewire chambers (372, 374) of the present example proximally extend from distal syringe end portion (324) and are transversely offset relative to each other. More particularly, vacuum and guidewire chambers (372, 374) respectively define longitudinal chamber axes in parallel with each other. Guidewire chamber (374) of the present example is shown as coaxial with the longitudinal lumen axis of needle lumen (22) whereas vacuum chamber (372) is transversely offset from the longitudinal lumen axis of needle lumen (22) while access needle (14) is secured to syringe (18).

Distal syringe end portion (324) further includes a conduit (376) distally extending to a distal syringe opening (378), which is surrounded by female luer lock (44) in the present example. Conduit (376) connects each of vacuum and guidewire chambers (372, 374) to distal syringe opening (378) for further communication into needle lumen (22) during use. More particularly, conduit (376) includes a distal lumen (380) directly connected to distal syringe opening (378), a proximal guidewire lumen (382) directly connected to guidewire chamber (374), and a proximal vacuum lumen (384) directly connected to vacuum chamber (372). Proximal guidewire lumen (382) and proximal vacuum lumen (384) distally extend from respective guidewire and vacuum chambers (374, 372) and intersect at distal lumen (380) in a Y-shaped configuration for communication with distal syringe opening (378), although it will be appreciated that any configuration for communicating fluid and/or guidewire (20) through distal syringe opening (378) may be similarly used.

In the proximal guidewire position, distal guidewire tip (116) remains transversely surrounded by access needle (14) within needle lumen (22), whereas distal guidewire tip (116) protrudes from access needle (14) in the distal guidewire position. As noted above, handle (104) pushes or pulls guidewire (20) as directed by the operator while handle (104) and annular fluid seal (110) retain a portion of guidewire body (114) along the chamber axis within guidewire chamber (74) and the longitudinal lumen axis of needle lumen (22). Guidewire body (114) is thus retained along a common, longitudinally extending axis from distal needle tip (34) to handle (104), regardless of being in the distal or proximal guidewire position in order to further inhibit catching, snagging, twisting, bending, or kinking of guidewire (20) during movement.

Figure 10:
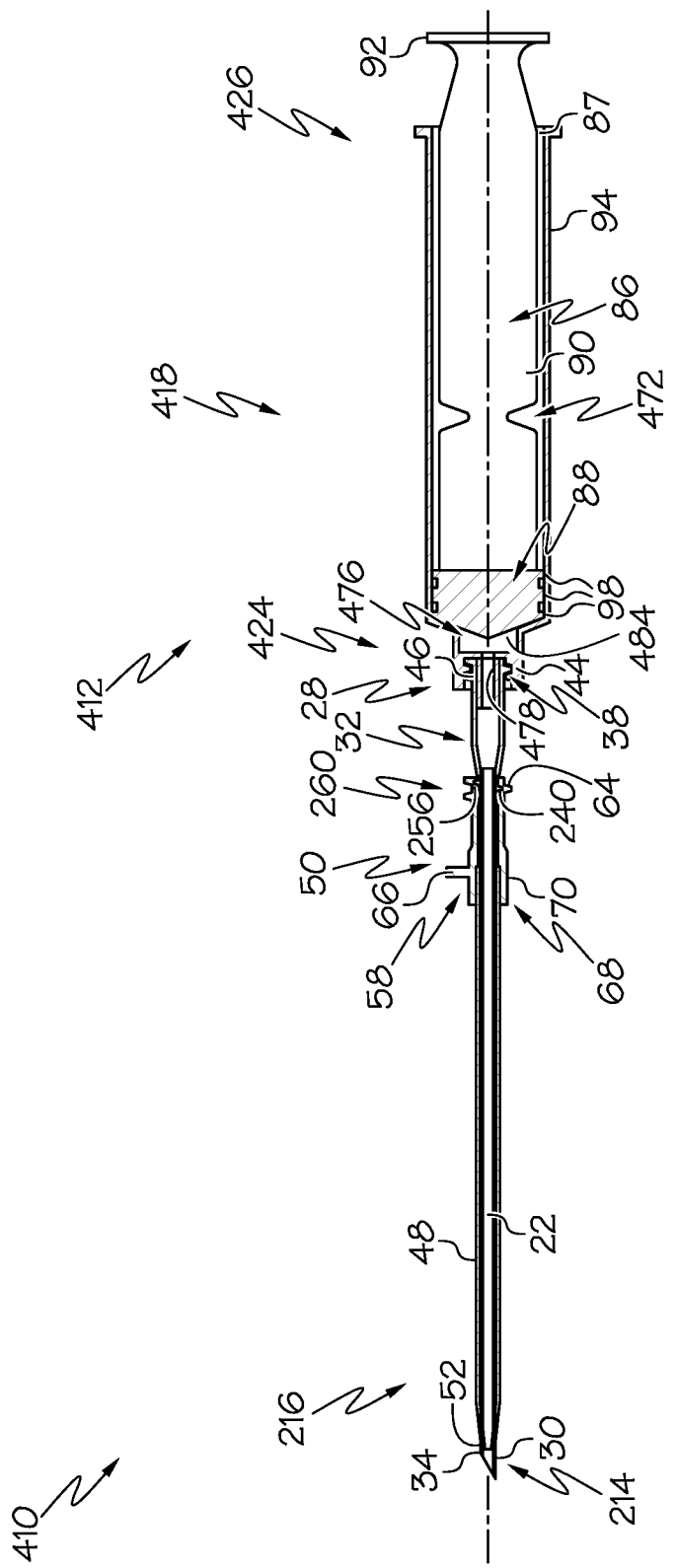
FIG. 10 depicts a cross-sectional view of a fourth exemplary embodiment of a catheter system taken along a centerline thereof including the pliable catheter and the access needle of FIG. 7 and a third example of a syringe for introducing the pliable catheter into a patient.

FIG. 10 shows a fourth exemplary embodiment of a catheter system (410) having access needle (214) and pliable catheter (216) discussed above in greater detail for use with a third example of a syringe assembly (412). Rather than having vacuum chamber (72) (see FIG. 4) in conjunction with guidewire chamber (72) (see FIG. 4), syringe assembly (412) does not include any such guidewire chamber, such as guidewire chamber (72) (see FIG. 4). Furthermore, syringe assembly (412) also does not include a guidewire, such as guidewire (20) (see FIG. 4), a handle, such as handle (104), nor other guidewire related features discussed above. In some instances, such syringe assembly (412) without guidewire (20) (see FIG. 4) may be beneficial, such as for greater simplicity of syringe and/or procedure during use and/or for reduced system costs. Unless otherwise stated herein, catheter system (410) has like structure for functioning as catheter system (10) (see FIG. 4) and/or catheter system (210) (see FIG. 7), and like numbers used below indicate like features discussed above in greater detail.

To this end, syringe (418) of syringe assembly (412) proximally extends from a distal syringe end portion (424) to a proximal syringe end portion (426). Vacuum chamber (472) of the present example proximally extends from distal syringe end portion (424) and defines a longitudinal chamber axis coaxially aligned with the longitudinal lumen axis of needle lumen (22). Distal syringe end portion (424) further includes a conduit (476) distally extending to a distal syringe opening (478), which is surrounded by female luer lock (44) in the present example. Conduit (476) connects vacuum chamber (472) to distal syringe opening (478) for further communication into needle lumen (22) during use. More particularly, conduit (476) includes a vacuum lumen (484) directly connected to vacuum chamber (472). Vacuum lumen (484) distally extends from vacuum chamber (472) and intersects at distal syringe opening (478) in a linear configuration for communication therewith, although it will be appreciated that any configuration for communicating fluid may be similarly used.

II. METHOD OF INTRODUCING AN IV CATHETER INTO A PATIENT

Each of catheter systems (10, 210, 310, 410) shown in FIGS. 1-10 are configured for placing pliable catheters (16, 216) through a skin (150) of a patient (152) and into an anatomy, such as a central vein (154), including but not limited to an internal jugular vein, a femoral vein, or a subclavian vein. For example, catheter systems (10, 210, 310, 410) may be used to access the internal jugular (i.e., neck) vein or femoral (i.e., groin) vein. However, the femoral vein is often deeper, so it may be beneficial for catheter systems (10, 210, 310, 410) to be compatible with longer access needles (not shown) and longer pliable catheters (not shown) relative to those used to access an internal jugular vein. Body habitus may also affect the desirable length of various components of catheter systems (10, 210, 310, 410). The following will describe the use of such catheter systems (10, 210, 310, 410) with respect to the first exemplary catheter system (10) of FIGS. 1-6, but it will be appreciated that such description similarly applies to catheter systems (210, 310, 410) (see FIGS. 7-10).

Figure 11:
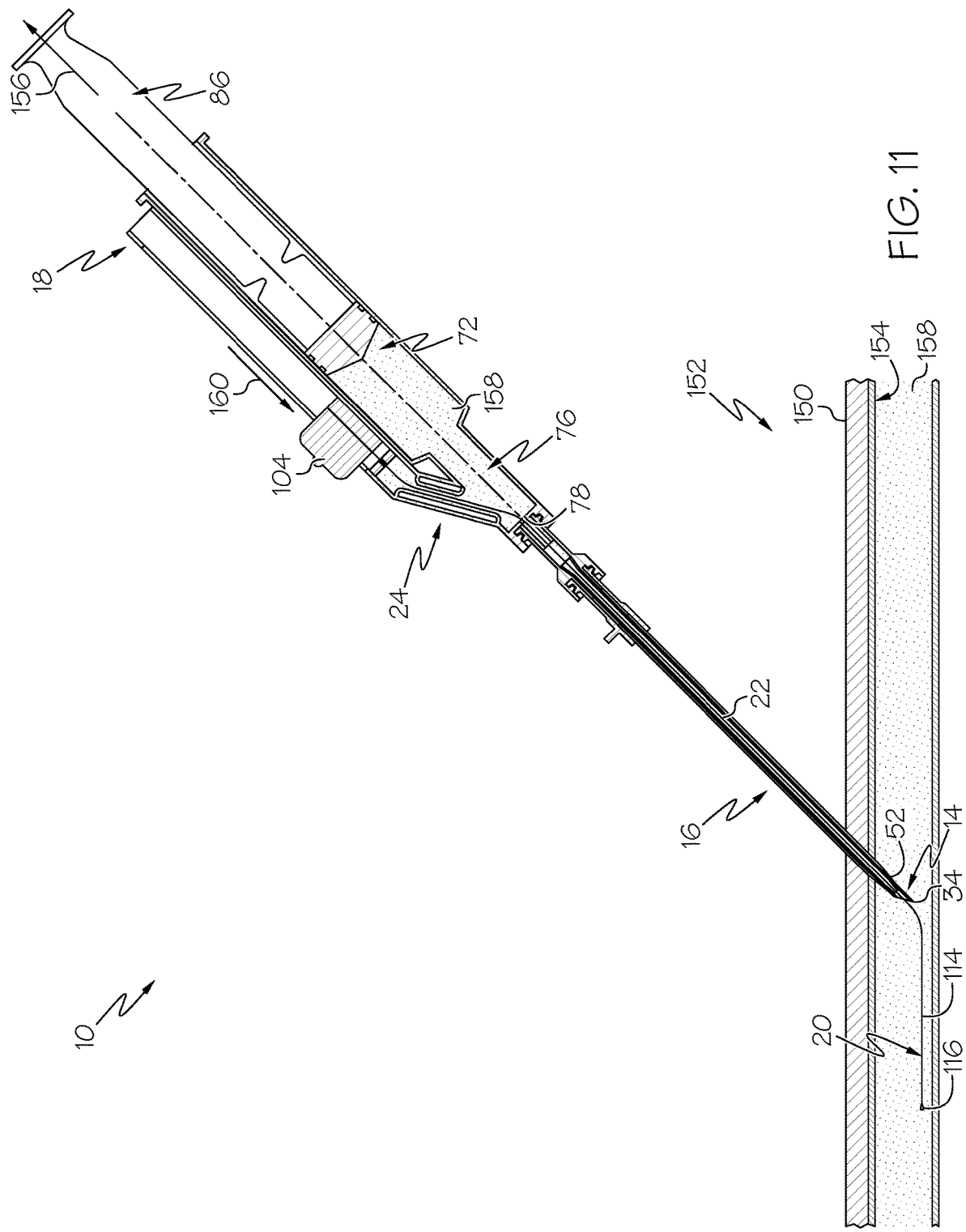
FIG. 11 depicts a sectional view of the catheter system of FIG. 1 having the access needle inserted into a central vein and a guidewire being urged along the access needle and further into the central vein.

In use, with respect to FIG. 11, the operator grips catheter system (10) about syringe (18) and manipulates syringe (18)

with pliable catheter (16) pre-loaded over access needle (14) such that distal needle tip (34) contacts the skin (150) in alignment with the central vein (154) as desired by the operator. With guidewire (20) still in the proximal guidewire position, the operator then distally urges an entirety of catheter system (10) toward the patient (152) such that distal needle tip (34) punctures through the skin (150) and the central vein (154) and further inserts distal needle tip (34) into the central vein (154). During insertion, pliable catheter (16) remains relatively rigid being secured on access needle (14) and is similarly inserted through the skin (150) and central vein (154) such that distal catheter tip (52) is also positioned within the central vein (154).

Once the operator enters the skin (15) and underlying soft tissues and distal needle tip (34) and distal catheter tip (52) are positioned in these tissues and being directed towards central vein (154), the operator selectively and proximally withdraws vacuum plunger (86) through vacuum chamber (72) as indicated by arrow (156) in order to generate a vacuum in vacuum chamber (72) and draw blood (158) from central vein (154). Such drawn blood (158) proximally flows along needle lumen (22), through distal syringe opening (78) and conduit (76), and collects within vacuum chamber (72). The collected drawn blood (158) in vacuum chamber (72) provides an indication to the operator that distal needle tip (34) and distal catheter tip (52) are fluidly connected to central vein (154) for confirming the desired placement of syringe system (10). In the event that another bodily fluid other than the desired bodily fluid is drawn into vacuum chamber (72), this collected fluid provides an alternative indication to that the operator that distal needle tip (34) and distal catheter tip (52) are not in the desired placement. The operator may thus remove catheter system (10) from the patient (152) and repeat insertion of distal needle tip (34) and distal catheter tip (52) through the skin (150) at another location on the patient (152) for one or more repeated attempts at the desired placement of syringe system (10) as needed. Alternatively or in addition, the operator may use ultrasound for confirmation of distal needle tip (34) and distal catheter tip (52) in the desired placement for vascular access.

With the distal needle tip (34) and distal catheter tip (52) positioned in the central vein (154), the operator grips handle (104) and slides handle (104) from the proximal guidewire position toward the distal guidewire position as indicated by an arrow (160). In turn, guidewire body (114), with distal guidewire tip (116), distally slides through syringe (18) and needle lumen (22) such that distal guidewire tip (116) exits from within needle lumen (22) and into the central vein (154) as shown in FIG. 11. A distal portion of guidewire body (114), including distal guidewire tip (116), thus distally projects from access needle (14) and pliable catheter (16).

Figure 12:
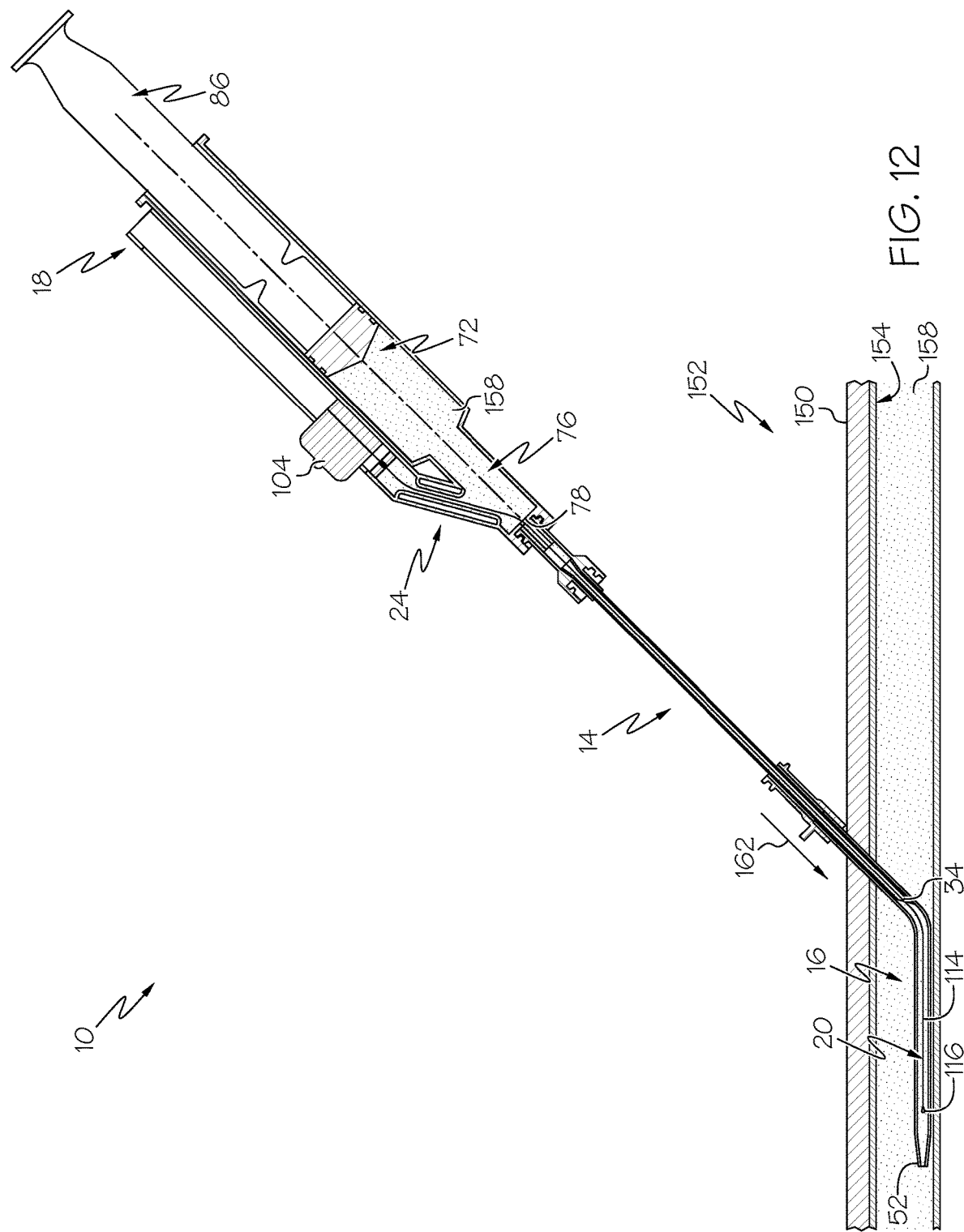
FIG. 12 depicts the sectional view of the catheter system similar to FIG. 11, but showing the pliable catheter being urged along the access needle and further into the central vein such that the central vein is positioned to be accessed for use.

With respect to FIG. 12, the operator then rotates pliable catheter (16) relative to access needle (14) a predetermined rotation (e.g., ¼ revolution, ½ revolution, ⅛ revolution, etc.) to unlock pliable catheter (16) from access needle (14) such that pliable catheter (16) is longitudinally released from distal syringe end portion (24). The operator grips projections (66) and distally urges pliable catheter (16) away from distal syringe end portion (24) and toward the patient (152) as indicated by an arrow (162), thereby introducing pliable catheter (16) further into central vein (154). During this introduction of pliable catheter (16), access needle (14) and the distal portion of guidewire body (114), including distal guidewire tip (116), guide pliable catheter (16) into the desired position within the central vein (154). Pliable catheter (16) continues to slide off of access needle (14) and flex in order to bend to the shape of the central vein (154). In one example, the operator then returns guidewire (20) to the proximal guidewire position and proximally withdraws any remaining distal portion of access needle (14) from within pliable catheter (16) and discards access needle (14) and syringe assembly (12). In another example, guidewire (20) simply remains in the distal guidewire position while the operator proximally withdraws any remaining distal portion of access needle (14) from within pliable catheter (16) and discards access needle (14) and syringe assembly (12). Pliable catheter (16) thus remains placed in the desired position in fluid connection with the central vein (154) for access to the central vein (154) as a central venous catheter.

In order to further facilitate placement of pliable catheter (16) for vascular access, a small amount of lubricant may be applied to coat pliable catheter (16) and/or access needle (14). Moreover, the operator may view any of the indicia (105, 71) on pliable catheter (16) or syringe (18) for additional understanding of the positioning of syringe assembly (12) relative to the patient (152).

In accordance with the above example, catheter system (10) allows for successful central vein access with less steps and time as compared to a classic central line. For example, catheter system (10) has a relatively compact design with a pre-loaded pliable catheter (16) and smooth, single action advancement of guidewire (20) connected conveniently together by syringe (18) with an increased likelihood of maintaining sterility during use. In one example, the relative size of the catheter system (10) as well as a lack of an otherwise longer catheter (e.g., as compared to conventional central lines which are typically about 20 centimeters in length) and separate guidewire allow pliable catheter (16) to be placed under sterile conditions without requiring a full sterile gown, although such a gown may be optionally worn in some circumstances. Moreover, a locking dressing (not shown) may be applied at the puncture site via catheter system (10) as discussed briefly above, thereby reducing, or even eliminating suturing of pliable catheter (16) in place. While local anesthesia may be used in some examples, local anesthesia may not be used in other examples for awake patients as there is only a single puncture by access needle (14) without the use of a large dilator. Furthermore, the compact design of catheter system (10) may be beneficial outside of a hospital, such as during community ground and helicopter transport of critically ill patients with physicians and advanced practice providers on board as well as tactical combat casualty care. Of course, it will be appreciated catheter system (10) may be used under any desired conditions for accessing an anatomy such that the invention is not intended to be limited to the conditions described herein.

By way of further example, variations of catheter system (10) could have several other applications for use. For instance, the operator may use catheter system (10) as an introducer for a classic triple lumen central line by performing the Seldinger technique in the event that such a technique is clinically required at a later time. Catheter system (10) may also be used to access any fluid or air-filled body cavity for placement of generally any tubular medical device. Various examples include alternative venous access, arterial access, or drainage of pleural, pericardial, or peritoneal fluid. Alternative catheters may also be used with syringe assembly (12) for different purposes. In one example, the operator may connect syringe assembly (12) to a preloaded pigtail catheter (not shown) for drainage and treatment of pneumothorax, pleural fluid, pericardial effusion, or ascites as desired. It will thus be appreciated that syringe assembly (12) may be used to perform various procedures such that the invention is not intended to be unnecessarily limited to the venous access described above in greater detail.

III. EXAMPLES

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A catheter system for accessing an anatomy of a patient, comprising: a syringe including a first chamber and a distal syringe end portion, wherein the distal syringe end portion defines a conduit distally extending to a distal syringe opening such that the conduit fluidly connects the first chamber to the distal syringe opening; an access needle defining a needle lumen longitudinally extending therethrough and secured relative to the distal syringe end portion such that the access needle distally projects from the distal syringe end portion; a pliable catheter releasably secured relative to the access needle such that the access needle is received within the pliable catheter; and a guidewire operatively connected to the syringe and distally extending through the conduit toward the distal syringe opening, wherein the guidewire is configured to selectively move through the conduit, the distal syringe opening, and along the needle lumen to thereby guide movement of the pliable catheter relative to the access needle for introducing the pliable catheter into the patient.

Example 2

The catheter system of Example 1, wherein the syringe further includes a second chamber in communication with the conduit, and wherein the guidewire extends from the second chamber and into the conduit.

Example 3

The catheter system of Example 2, wherein each of the first and second chambers is proximally positioned relative to the access needle and transversely offset from each other.

Example 4

The catheter system of any one or more of Examples 2 through 3, wherein each of the first and second chambers longitudinally extend in parallel with each other.

Example 5

The catheter system of any one or more of Examples 2 through 4, wherein the guidewire is configured to selectively and longitudinally translate through the second chamber to thereby selectively move the guidewire relative to the access needle.

Example 6

The catheter system of any one or more of Examples 2 through 5, wherein the syringe further includes a plunger movably received within the first chamber such that selective withdrawal of the plunger from the first chamber is configured to generate a vacuum at the distal syringe opening.

Example 7

The catheter system of Example 6, wherein the plunger is configured to selectively and longitudinally translate through the first chamber to withdraw the plunger from the first chamber.

Example 8

The catheter system of any one or more of Examples 1 through 7, wherein the needle lumen extends along a longitudinal axis, and wherein the longitudinal axis aligns with the first chamber.

Example 9

The catheter system of Example 8, wherein the first chamber is coaxial with the longitudinal axis.

Example 10

The catheter system of any one or more of Examples 1 through 7, wherein the needle lumen extends along a longitudinal axis, and wherein the longitudinal axis aligns with the second chamber.

Example 11

The catheter system of Example 10, wherein the guidewire in the second chamber is coaxial with the longitudinal axis.

Example 12

The catheter system of any one or more of Examples 2 through 11, wherein the conduit of the distal syringe end portion includes a first proximal lumen, a second proximal lumen, and a distal lumen fluidly connected to the distal syringe opening, wherein the first and second proximal lumens respectively communicate with the first and second chamber and intersect at the distal lumen for communicating fluid and the guidewire through the distal syringe opening.

Example 13

The catheter system of Example 12, wherein the syringe further includes a fluid seal positioned in the second proximal lumen, wherein the fluid seal is configured to moveably receive the guidewire therethrough while inhibiting a bodily fluid from being introduced into the second chamber.

Example 14

The catheter system of any one or more of Examples 1 through 13, wherein the guidewire has a distal wire tip, and wherein the guidewire is configured to selectively move from a proximal guidewire position to a distal guidewire position, wherein the distal wire tip in the proximal guidewire position is positioned within the needle lumen, and wherein the distal wire tip in the distal guidewire position is positioned outside the needle lumen.

Example 15

The catheter system of Example 14, wherein the pliable catheter is configured to be released relative to the distal syringe end portion to thereby selectively and distally move the pliable catheter relative to the access needle, and wherein the guidewire in the distal guidewire position is configured to guide selective and distal movement of the pliable catheter relative to the access needle for introducing the pliable catheter into the patient.

Example 16

A kit catheter system for accessing an anatomy of a patient, comprising: a syringe including a first chamber and a distal syringe end portion, wherein the distal syringe end portion defines a conduit distally extending to a distal syringe opening such that the conduit fluidly connects the first chamber to the distal syringe opening; an access needle defining a needle lumen and configured to releasably secure relative to the distal syringe end portion such that the access needle distally projects from the distal syringe end portion; a pliable catheter configured to be releasably secured relative to the access needle such that the access needle is received within the pliable catheter; and a guidewire operatively connected to the syringe and distally extending through the conduit toward the distal syringe opening, wherein the guidewire is configured to selectively move through the conduit and the distal syringe opening and along the needle lumen to thereby guide movement of the pliable catheter relative to the access needle for introducing the pliable catheter into the patient.

Example 17

A method of introducing a pliable catheter into a patient with a catheter system, wherein the catheter system includes a syringe having a first chamber and a distal syringe end portion, wherein the distal syringe end portion defines a conduit distally extending to a distal syringe opening such that the conduit fluidly connects the first chamber to the distal syringe opening; an access needle defining a needle lumen longitudinally extending therethrough and secured relative to the distal syringe end portion such that the access needle distally projects from the distal syringe end portion; the pliable catheter releasably secured relative to the access needle such that the access needle is received within the pliable catheter; and a guidewire operatively connected to the syringe and distally extending through the conduit toward the distal syringe opening, wherein the guidewire is configured to selectively move through the conduit, the distal syringe opening, and along the needle lumen, the method comprising: guiding the pliable catheter distally along the guidewire thereby introducing the pliable catheter into an anatomy of the patient.

Example 18

The method of Example 17, further comprising distally moving a distal wire tip of the guidewire from a proximal guidewire position within the needle lumen to a distal guidewire position outside of the needle lumen and into the anatomy.

Example 19

The method of any one or more of Example 18, further comprising: generating a vacuum within the conduit thereby drawing a bodily fluid from the anatomy through the needle lumen and into the syringe; and confirming access to the anatomy based on the bodily fluid drawn into the syringe.

Example 20

The method of Example 19, wherein the anatomy is a central vein and the bodily fluid is a blood from the central vein.

Example 21

A catheter system for accessing an anatomy of a patient, comprising: a syringe including a first chamber and a distal syringe end portion, wherein the distal syringe end portion defines a conduit distally extending to a distal syringe opening such that the conduit fluidly connects the first chamber to the distal syringe opening; an access needle defining a needle lumen longitudinally extending therethrough and secured relative to the distal syringe end portion such that the access needle distally projects from the distal syringe end portion; and a pliable catheter releasably secured relative to the access needle such that the access needle is received within the pliable catheter, wherein the pliable catheter is configured to be released relative to the access needle such that the access needle guides movements of the pliable catheter for introducing the pliable catheter into the patient.

Example 22

A kit catheter system for accessing an anatomy of a patient, comprising: a syringe including a first chamber and a distal syringe end portion, wherein the distal syringe end portion defines a conduit distally extending to a distal syringe opening such that the conduit fluidly connects the first chamber to the distal syringe opening; an access needle defining a needle lumen and configured to releasably secure relative to the distal syringe end portion such that the access needle distally projects from the distal syringe end portion; and a pliable catheter configured to be releasably secured relative to the access needle such that the access needle is received within the pliable catheter, wherein the pliable catheter is configured to be released relative to the access needle such that the access needle guides movements of the pliable catheter for introducing the pliable catheter into the patient.

Example 23

A method of introducing a pliable catheter into a patient with a catheter system, wherein the catheter system includes a syringe having a first chamber and a distal syringe end portion, wherein the distal syringe end portion defines a conduit distally extending to a distal syringe opening such that the conduit fluidly connects the first chamber to the distal syringe opening; an access needle defining a needle lumen longitudinally extending therethrough and secured relative to the distal syringe end portion such that the access needle distally projects from the distal syringe end portion; and the pliable catheter releasably secured relative to the access needle such that the access needle is received within the pliable catheter, wherein the pliable catheter is configured to be released relative to the access needle such that the access needle guides movements of the pliable catheter for introducing the pliable catheter into the patient, the method comprising: guiding the pliable catheter distally along the access needle thereby introducing the pliable catheter into an anatomy of the patient.

IV. MISCELLANEOUS

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

What is claimed is:

1. A catheter system for accessing an anatomy of a patient, comprising:
   a syringe including a first chamber and a distal syringe end portion, wherein the distal syringe end portion defines a conduit distally extending to a distal syringe opening such that the conduit fluidly connects the first chamber to the distal syringe opening;
   an access needle defining a needle lumen longitudinally extending therethrough and secured relative to the distal syringe end portion such that the access needle distally projects from the distal syringe end portion;
   a pliable catheter releasably secured relative to the access needle such that the access needle is received within the pliable catheter;
   a guidewire operatively connected to the syringe and distally extending through the conduit toward the distal syringe opening, wherein the guidewire is configured to selectively move through the conduit, the distal syringe opening, and along the needle lumen to thereby guide movement of the pliable catheter relative to the access needle for introducing the pliable catheter into the patient; and
   a fluid seal positioned in the conduit such that the guidewire movably extends therethrough and such that the fluid seal fluidly seals the conduit about the fluid seal while the guidewire extends through the fluid seal thereby inhibiting a bodily fluid from proximally moving from the conduit and beyond the fluid seal, wherein the guidewire is movably secured relative to the syringe such that the guidewire remains proximate to the syringe during use.

2. The catheter system of claim 1, wherein the syringe further includes a second chamber in communication with the conduit, and wherein the guidewire extends from the second chamber and into the conduit.

3. The catheter system of claim 2, wherein the conduit of the distal syringe end portion includes a first proximal lumen, a second proximal lumen, and a distal lumen fluidly connected to the distal syringe opening, wherein the first and second proximal lumens respectively communicate with the first and second chamber and intersect at the distal lumen for communicating fluid and the guidewire through the distal syringe opening.

4. The catheter system of claim 3, wherein the fluid seal is positioned in the second proximal lumen, wherein the fluid seal is configured to moveably receive the guidewire therethrough while inhibiting the bodily fluid from being introduced into the second chamber.

5. The catheter system of claim 2, wherein each of the first and second chambers is proximally positioned relative to the access needle and transversely offset from each other.

6. The catheter system of claim 5, wherein the needle lumen extends along a longitudinal axis, and wherein the longitudinal axis of the needle lumen aligns with the first chamber.

7. The catheter system of claim 6, wherein the first chamber is coaxial with the longitudinal axis of the needle lumen.

8. The catheter system of claim 5, wherein the needle lumen extends along a longitudinal axis, and wherein the longitudinal axis of the needle lumen aligns with the second chamber.

9. The catheter system of claim 8, wherein the guidewire in the second chamber is coaxial with the longitudinal axis of the needle lumen.

10. The catheter system of claim 5, wherein each of the first and second chambers longitudinally extend in parallel with each other.

11. The catheter system of claim 10, wherein the guidewire is configured to selectively and longitudinally translate through the second chamber to thereby selectively move the guidewire relative to the access needle.

12. The catheter system of claim 11, wherein the syringe further includes a plunger movably received within the first chamber such that selective withdrawal of the plunger from the first chamber is configured to generate a vacuum at the distal syringe opening.

13. The catheter system of claim 12, wherein the plunger is configured to selectively and longitudinally translate through the first chamber to withdraw the plunger from the first chamber.

14. The catheter system of claim 1, wherein the guidewire has a distal wire tip, and wherein the guidewire is configured to selectively move from a proximal guidewire position to a distal guidewire position, wherein the distal wire tip in the proximal guidewire position is positioned within the needle lumen, and wherein the distal wire tip in the distal guidewire position is positioned outside the needle lumen.

15. The catheter system of claim 14, wherein the pliable catheter is configured to be released relative to the distal syringe end portion to thereby selectively and distally move the pliable catheter relative to the access needle, and wherein the guidewire in the distal guidewire position is configured to guide selective and distal movement of the pliable catheter relative to the access needle for introducing the pliable catheter into the patient.

16. The catheter system of claim 1, further comprising a fixation surface and wherein the syringe further includes a second chamber with the fixation surface movably positioned and captured therein, wherein the second chamber is in communication with the conduit such that the guidewire extends from the second chamber and into the conduit, and wherein at least a portion of the guidewire is fixed to the fixation surface within the second chamber such that the at least the portion of the guidewire is captured within the second chamber.

17. The catheter system of claim 16, further comprising a handle having the fixation surface thereon such that at least a portion of the handle is captured in the second chamber, wherein the handle projects from the second chamber and is configured to be manipulated to thereby selectively direct movement of the at least the portion of the guidewire fixed thereto.

18. The catheter system of claim 16, wherein the at least the portion of the guidewire is fluidly sealed within the second chamber for maintaining sterility of the at least the portion of the guidewire during use.

19. The catheter system of claim 1, further comprising a handle fixed to the guidewire and movably secured relative to the syringe.

20. A kit catheter system for accessing an anatomy of a patient, comprising:
   a syringe including a first chamber and a distal syringe end portion, wherein the distal syringe end portion defines a conduit distally extending to a distal syringe opening such that the conduit fluidly connects the first chamber to the distal syringe opening;
   an access needle defining a needle lumen and configured to releasably secure relative to the distal syringe end portion such that the access needle distally projects from the distal syringe end portion;
   a pliable catheter configured to be releasably secured relative to the access needle such that the access needle is received within the pliable catheter;
   a guidewire operatively connected to the syringe and distally extending through the conduit toward the distal syringe opening, wherein the guidewire is configured to selectively move through the conduit and the distal syringe opening and along the needle lumen to thereby guide movement of the pliable catheter relative to the access needle for introducing the pliable cathter into the patient; and
   a fluid seal positioned in the conduit such that the guidewire movably extends therethrough and such that the fluid fluidly seals the conduit about the fluid seal while the guidewire extends through the fluid seal thereby a bodily fluid from proximally moving from the conduit and beyond the fluid seal,
   wherein the guidewire is movably secured relative to the syringe such that the guidewire remains proximate to the syringe during use.

21. A method of introducing a pliable catheter into a patient with a catheter system, wherein the catheter system includes a syringe having a first chamber and a distal syringe end portion, wherein the distal syringe end portion defines a conduit distally extending to a distal syringe opening such that the conduit fluidly connects the first chamber to the distal syringe opening; an access needle defining a needle lumen longitudinally extending therethrough and secured relative to the distal syringe end portion such that the access needle distally projects from the distal syringe end portion; the pliable catheter releasably secured relative to the access needle such that the access needle is received within the pliable catheter; a guidewire operatively connected to the syringe and distally extending through the conduit toward the distal syringe opening, wherein the guidewire is configured to selectively move through the conduit, the distal syringe opening, and along the needle lumen; and a fluid seal positioned in the conduit such that the guidewire movably extends therethrough and such that the fluid seal fluidly seals the conduit about the fluid seal while the guidewire extends through the fluid seal, wherein the guidewire is movably secured relative to the syringe such that the guidewire remains proximate to the syringe during use, the method comprising:
   guiding the pliable catheter distally along the guidewire thereby introducing the pliable catheter into an anatomy of the patient; and
   distally moving the guidewire through the fluid seal while the fluid seal is fluidly sealed thereagainst thereby inhibiting a bodily fluid from proximally moving from the conduit and beyond the fluid seal while the guidewire extends through the fluid seal.

22. The method of claim 21, further comprising distally moving a distal wire tip of the guidewire from a proximal guidewire position within the needle lumen to a distal guidewire position outside fo the needle lumen and into the anatomy.

23. The method of claim 22, further comprising:
   generating a vacuum within the conduit thereby drawing a bodily fluid from the anatomy through the needle lumen and into the syringe; and
   confirming access to the anatomy based on the bodily fluid drawn into the syringe.

* * * * *

UNITED STATES PATENT AND TRADEMARK OFFICE
CERTIFICATE OF CORRECTION

PATENT NO.        : 10,898,689 B2  
APPLICATION NO.   : 16/675569  
DATED             : January 26, 2021  
INVENTOR(S)       : Zachary Holt Page 1 of 1

It is certified that error appears in the above-identified patent and that said Letters Patent is hereby corrected as shown below:

In the Claims

Column 21, Claim 20, Line 44, reads "… access needle for introducing the pliable cathter into the …"; which should be deleted and replaced with "… access needle for introducing the pliable catheter into the …"

Column 21, Claim 20, Line 47, reads "… the fluid fluidly seals the conduit about the fluid seal …"; which should be deleted and replaced with "… the fluid seal fluidly seals the conduit about the fluid seal …"

Column 22, Claim 20, Line 1, reads "… thereby a bodily fluid from proximally moving from the …"; which should be deleted and replaced with "… thereby inhibiting a bodily fluid from proximally moving from the …"

Column 22, Claim 22, Line 40, reads "… guidewire position outside fo the needle lumen and into the …"; which should be deleted and replaced with "… guidewire position outside of the needle lumen and into the …"

Signed and Sealed this  
Twenty-third Day of March, 2021

Drew Hirshfeld  
*Performing the Functions and Duties of the*  
*Under Secretary of Commerce for Intellectual Property and*  
*Director of the United States Patent and Trademark Office*